US008403919B2

(12) United States Patent
Campin et al.

(10) Patent No.: US 8,403,919 B2
(45) Date of Patent: Mar. 26, 2013

(54) NOMOGRAM COMPUTATION AND APPLICATION SYSTEM AND METHOD FOR REFRACTIVE LASER SURGERY

(75) Inventors: John A. Campin, Orlando, FL (US); George H. Pettit, Maitland, FL (US)

(73) Assignee: Alcon Refractivehorizons, Inc., Fort Worth, TX (US)

( * ) Notice: Subject to any disclaimer, the term of this patent is extended or adjusted under 35 U.S.C. 154(b) by 1664 days.

(21) Appl. No.: 11/758,425

(22) Filed: Jun. 5, 2007

(65) Prior Publication Data

US 2008/0306573 A1    Dec. 11, 2008

(51) Int. Cl.
*A61B 18/18*    (2006.01)
(52) U.S. Cl. ..................... 606/5; 606/4; 606/6
(58) Field of Classification Search .................. None
See application file for complete search history.

(56) References Cited

U.S. PATENT DOCUMENTS

| 2003/0133075 A1* | 7/2003 | Sheets et al. | 351/212 |
| 2004/0054358 A1* | 3/2004 | Cox et al. | 606/5 |
| 2007/0115432 A1* | 5/2007 | Thibos | 351/246 |

FOREIGN PATENT DOCUMENTS

| EP | 1327948 B1 | 12/2006 |
| WO | 03/060568 A2 | 7/2003 |
| WO | 2006/108250 A1 | 10/2006 |
| WO | 2007/078553 A2 | 7/2007 |

OTHER PUBLICATIONS

Kezirian et al. "Optimized Nomograms for Improved LASIK Outcomes" The Refractive Surgery Consultant 2002. American Academy of Ophthalmology Course Handout. Nov. 11, 2001. Accessed Mar. 5, 2012 at url: <http://www.surgivision.net/surgivisionpublic/apps/rsc/httpdocs/AAOCourseHandout.pdf>.*

"7.1.4. What are Confidence Intervals?", NIST/SEMATECH e-Handbook of Statistical Methods, http://www.itl.nist.gov/div898/handbook/prc/section1/prc14.htm, Created Jun. 1, 2003, Accessed Nov. 18, 2012.*

* cited by examiner

*Primary Examiner* — Bill Thomson
*Assistant Examiner* — Davin K Sands
(74) *Attorney, Agent, or Firm* — Keiko Ichiye

(57) ABSTRACT

A method for optimizing a prescription for laser-ablation corneal treatment includes receiving a measured correction prescription for a current patient. Next a database of treatment outcomes on a plurality of previously treated patients is accessed. The database contains a desired correction, and an actual correction. A difference between the desired correction and the actual correction represents an over- or undercorrection resulting from surgery. From the difference data is calculated a distribution of data points as a function of correction level. From the data-point distribution is calculated a statistically based offset applicable to the correction prescription for matching actual corrections with desired corrections. From the data-point distribution is calculated a confidence interval of the data using a predetermined confidence level. The statistically based offset is then adjusted based upon the confidence interval to provide an optimized prescription. The adjusted offset is then output for use in performing a refractive procedure.

17 Claims, 3 Drawing Sheets

NOMOGRAM COMPUTATION AND APPLICATION SYSTEM AND METHOD FOR REFRACTIVE LASER SURGERY

BACKGROUND OF THE INVENTION

1. Field of Invention

The present invention relates to systems and methods for performing refractive laser surgery on the eye, and, more particularly, to such systems and methods that adaptively modulate sensed data on the basis of data from prior procedures.

2. Description of Related Art

In conventional refractive laser surgery a clinician typically modifies a prescription entered into the treatment system. Such modifications are based upon prior experience with outcomes achieved with that particular treatment system, and also upon experience with particular patient populations derived from, for example, demographic data. For example, a surgeon might enter a 2-diopter myopic treatment prescription for a patient diagnosed with 3 diopters of myopia if analysis of previous outcomes indicates a 50% overcorrection using this system for patients of a particular category. Such an empirical alteration of entered treatment parameters based upon previous experience is referred to as a nomogram adjustment. Nomograms are considered essential by the ophthalmic community because different clinicians employ different surgical techniques, operate under different environmental conditions, have distinct patient demographics, etc.

One method of obtaining nomograms is to enter desired correction parameters into a laser system, measure a patient's refractive state (or errors) before and some time after the procedure, and then determine the achieved change in refraction as a function of desired change in refraction. By computing the relationship between these desired and achieved corrections, a surgeon can generate a nomogram that defines those adjustments to the values entered into the laser system that will result in the best achieved outcomes. Typically, this nomogram consists of equations that define the values to be entered into the laser system as a function of the desired correction and a plurality of patient parameters including, but not limited to, age and a variety of diagnostic measurements.

A standard way of computing and applying these corrections (nomograms) is to perform at least-squares fit, or other trend calculation, to the achieved versus desired correction data. However, this approach does not account for noise in the data, and can result in the computation of nomograms that are overly aggressive, with corresponding sub-optimal outcomes.

Therefore, it would be beneficial to provide a system and method for improving the calculation and application of nomograms, and hence, outcomes, for use with refractive laser surgery.

SUMMARY OF THE INVENTION

One aspect of the present invention is directed to a method for optimizing a prescription for laser-ablation corneal treatment. The method comprises the step of receiving a measured correction prescription for a current patient. Typically the prescription will have been obtained using a wavefront determination, although this is not intended as a limitation. Next a database of treatment outcomes on a plurality of previously treated patients is accessed. The database contains, for each previously treated patient, a preoperative wavefront-determined correction prescription, i.e., a desired correction, and a postoperative visual profile, i.e., an actual correction. A difference between the desired correction and the actual correction represents an over- or undercorrection resulting from the surgery.

A distribution of data points as a function of correction level is calculated from the difference data. A statistically based offset application to the correction prescription for matching actual corrections with desired corrections is then calculated from the data-point distribution. A confidence interval of the data using a predetermined confidence level is also calculated from the data-point distribution. The statistically based offset is then adjusted based upon the confidence interval to provide an optimized prescription. The adjusted statistically based offset is then output for use in performing a refractive procedure.

This embodiment of the method of the invention thus takes data distributions into account, so as to adjust the compensation factors, and thereby decreases the likelihood that noise and variation in the data will result in overly aggressive adjustments to the treated parameters. Thus the method has been show to provide improved outcomes with more with more stable nomograms.

Another embodiment of the present invention comprises a system for optimizing a prescription for laser-ablation corneal treatment comprising: a processor; a database of treatment outcomes on a plurality of previously treated patients, each treated patient outcome comprising a desired correction based upon the measured correction prescription and a postoperative actual correction, the database in signal communication with the processor; a software package resident on a medium readable by the processor, the software package comprising code segments adapted to: receive a measure correction prescription for a current patient; access the database of treatment outcomes; calculate from the accessed treatment outcomes a distribution of data points as a function of correction level; calculate from the data-point distribution a statistically based offset applicable to the correction prescription for matching actual corrections with desired corrections; calculate from the data-point distribution a confidence interval of the data using a predetermined confidence level; adjust the statistically based offset based upon the confidence interval to provide an optimized prescription; and output the adjusted offset for use in performing a refractive procedure. The code segment for calculating a statistically based offset can comprise a code segment for performing a least-squares fit or a code segment for performing a minimum least-squares error fit.

A further aspect includes a method for creating a system for optimizing a prescription for laser ablation surgery, which comprises the step of forming a database of treatment outcomes as described above. A search engine resident on a processor is adapted to extract treatment outcomes. Software is also provided for performing the calculational steps as outlined above.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the embodiments of the present invention will become more fully apparent as the description that now follows is read in conjunction with the accompanying drawing.

DETAILED DESCRIPTION OF THE PREFERRED EMBODIMENTS

Figure 1:
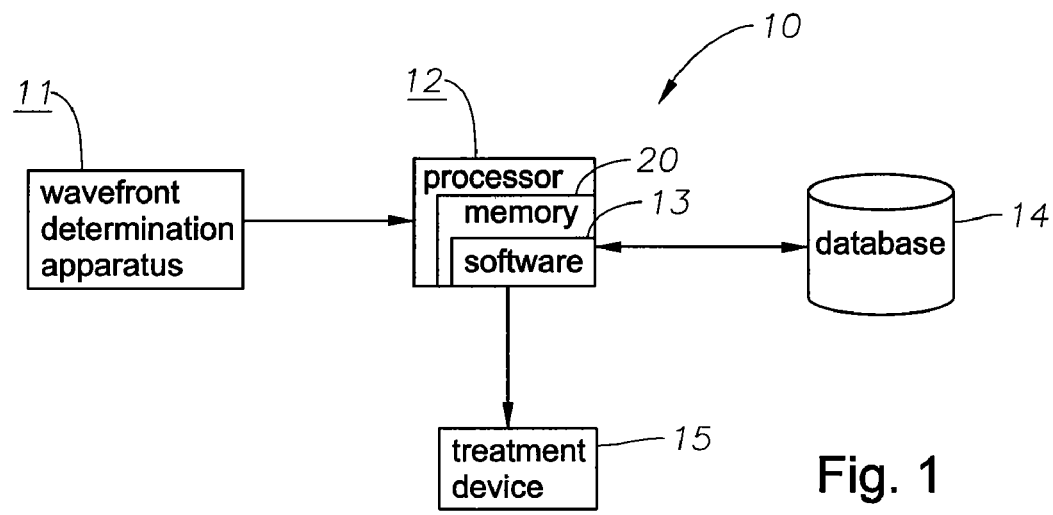
FIG. 1 is a schematic diagram of an embodiment of the system of the present invention.

A description of the preferred embodiments of the present invention will now be presented with reference to FIGS. 1-5.

A system 10 (FIG. 1) and method 100 (FIG. 2) of the present invention are directed to an optimization of a prescription for laser-ablation corneal treatment. In a preferred embodiment, a measured correction prescription will have been measured (block 101) using a wavefront determination apparatus 11 for a current patient. The raw correction prescription is received into a processor 12 having a memory 20 with a software package 13 (block 102) resident therein. Memory 20 can be any medium, as will be known to those having skill in the art, operable to be read by the processor 12 and operable to store software package 13. For example, memory 12 can be RAM, ROM, a magnetic hard drive or optical storage system.

A database 14 of treatment outcomes on a plurality of previously treated patient is accessed (block 103) by the software package 13. Each treated patient outcome has associated therewith a preoperative wavefront-determined correction prescription (a desired correction), and a postoperative visual profile (an actual correction).

From the treatment outcomes in the database 14, the software package 13 and processor 12 calculate a distribution of data points as a function of correction level (block 104). From the distribution is calculated a trend line, for example, using a minimum-least-squares error fit, between the desired and actual corrections (block 105), representing a statistically based offset applicable to the correction prescription for matching actual corrections with desired corrections.

From the distribution is also calculated a confidence interval of the data using a predetermined confidence level (block 106). Typical confidence levels can be in a range of 90-05%, for example, although this range is not intended as a limitation. If the confidence interval is sufficiently small (block 107), the calculated offset can be used to alter the input correction prescription (block 108); if the confidence interval is above a predetermined amount (block 107), the statistically based offset can be adjusted based upon the confidence interval to provide an optimized prescription (block 109), and output (block 110) for use in performing a refractive procedure (block 111), for example, to a treatment device 15.

Thus the current patient correction prescription is adjusted commensurate with the calculations of the present invention to form an optimized prescription using a computed confidence-based nomogram, thereby avoiding a statistically calculable over- or undercorrection, and accounting for noise and variation in the data.

It will be understood by one of skill in the art that this particular embodiment represents an exemplary method, and that alternate embodiments may be envisioned without departing from the spirit of the invention.

Preferably, following each treatment (block 111) of a current patient, a treatment outcome on the current patient is measured (block 112) at a predetermined interval following the treatment. In order to continuously enrich the database, the treatment outcome for the current patient is then entered into the database (block 113).

Figure 3:
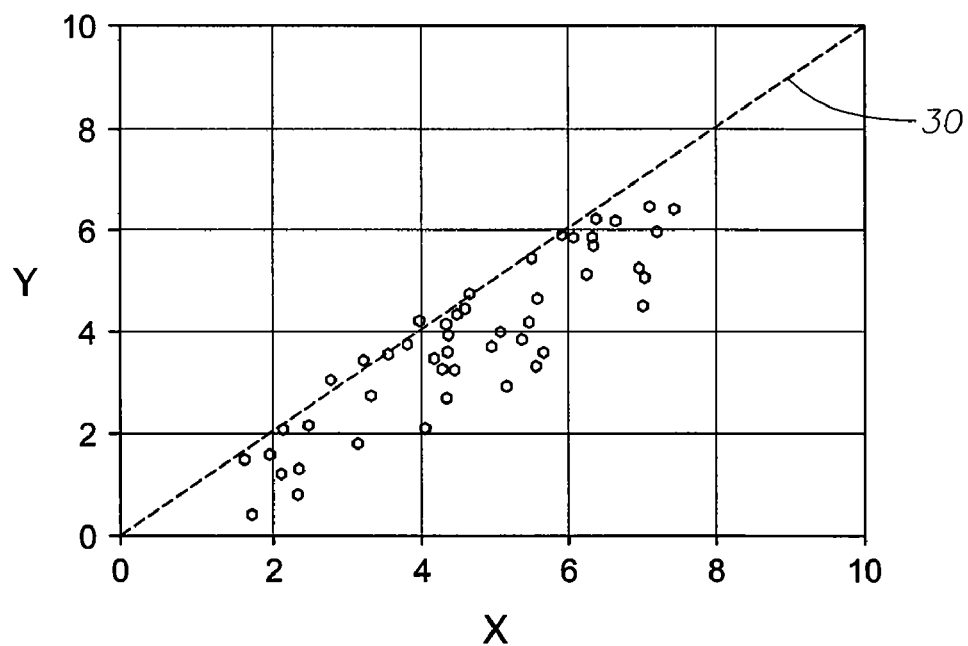
FIG. 3 is a graph of a sample data distribution of desired and actual corrections.
Figure 2:
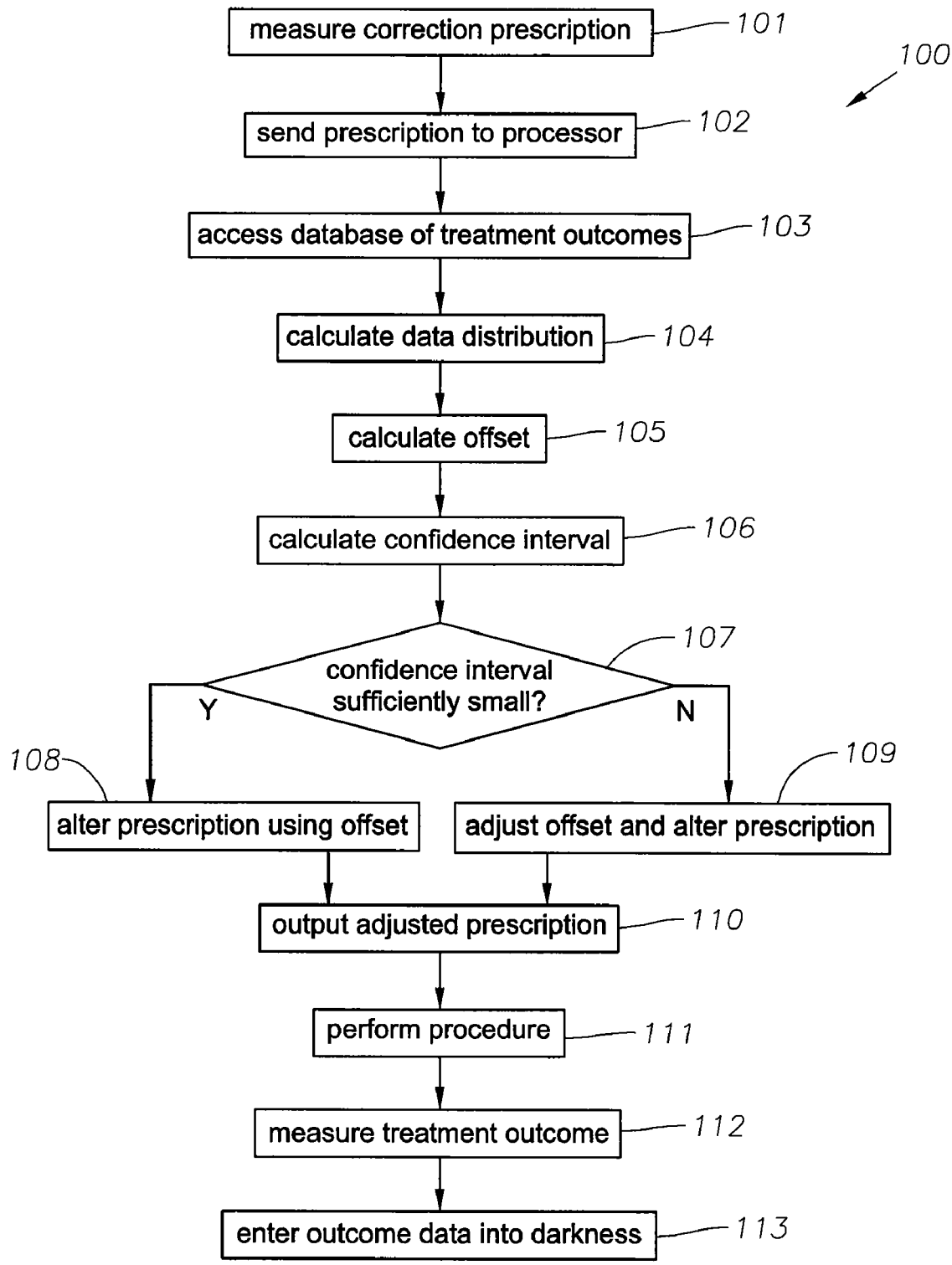
FIG. 2 is a flowchart of an embodiment of the method of the present invention for optimizing a treatment prescription for a current patient.
Figure 4:
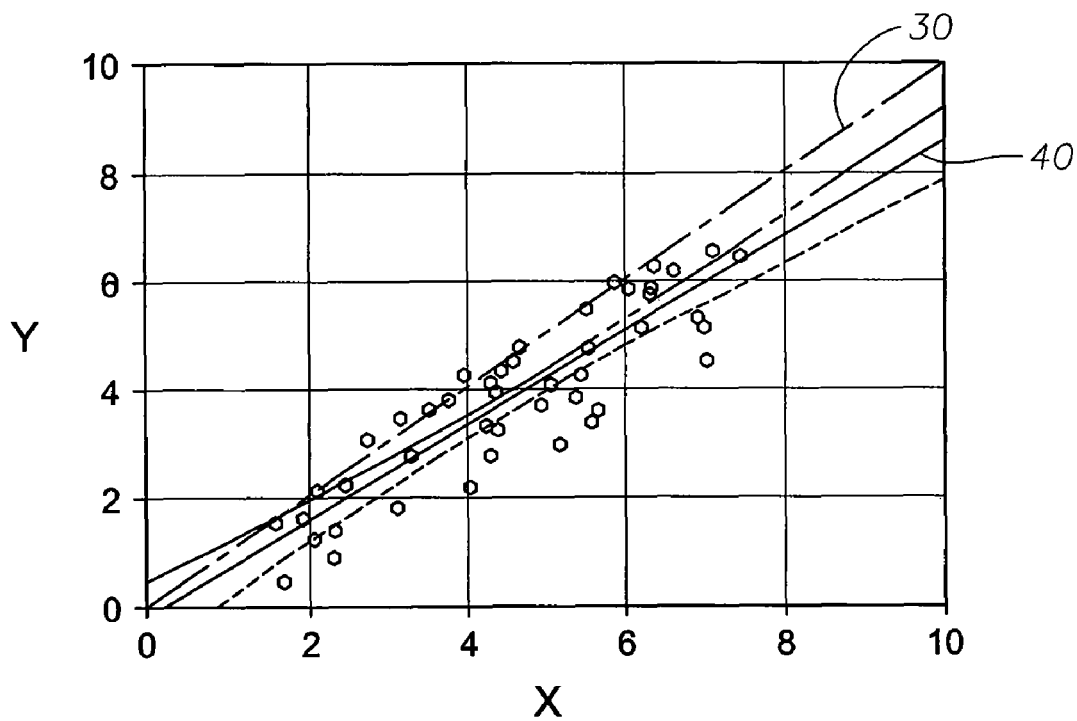
FIG. 4 is a graph including the same data distribution as in FIG. 3, and also including a trend line (solid line) calculated from a minimum least-squares-error fit, with 95% confidence intervals (dotted lines) surrounding the trend line.
Figure 5:
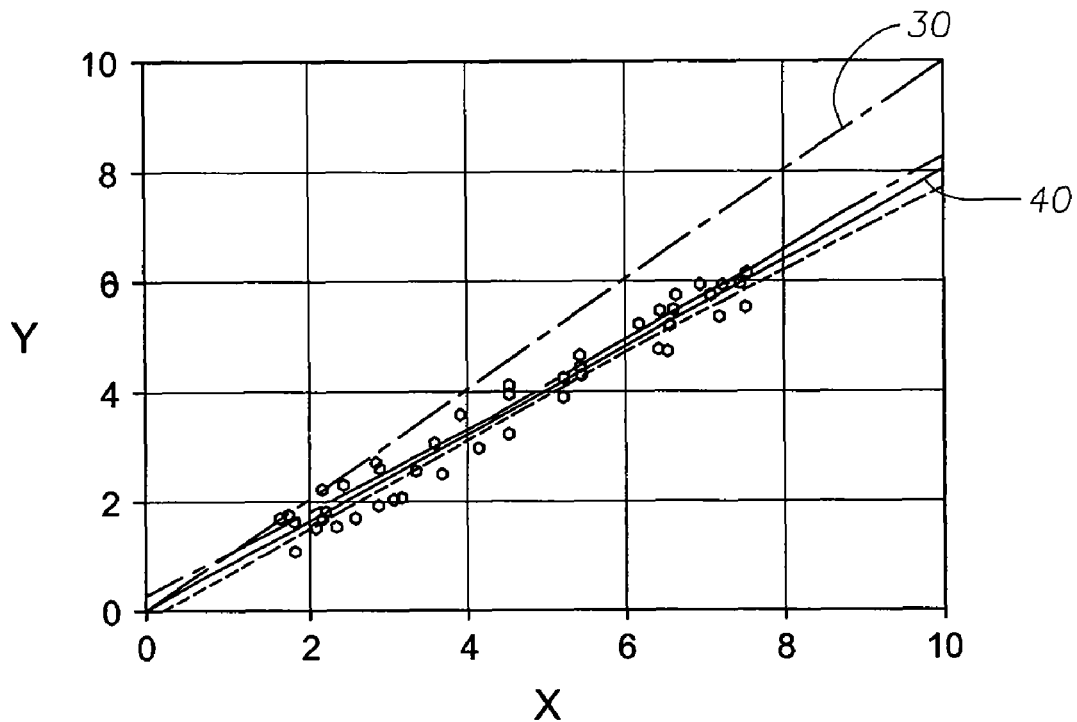
FIG. 5 is a graph of a sample data distribution for a different data set from that of FIG. 3, including a trend line (solid line) and 95% confidence interval lines (dotted lines).

Examples using two data sets are given in FIGS. 3-5. In FIG. 3 is graphed a sample data set in which the x-axis shows intended or desired corrections, and the y-axis plots the corresponding achieved corrections (in diopters). The dashed line 30 bisecting the graph indicates where all the data points would lie if the outcomes were perfect.

FIG. 4 shows the same data set, but adding a trend line 40 (solid) that has been calculated to best describe the data, using a minimum least-squares-error fit. The dotted lines surrounding the trend line represent the 95% confidence intervals.

FIG. 5 shows a different data set along with the corresponding best-fit (trend) line (solid) and the 95% confidence intervals (dotted lines surrounding the trend line). With these data, the average amount of deviation from perfect (dashed line 30) is similar to that in the data set of FIGS. 3 and 4; however, the data are now much "tighter"; that is, the data points are consistently closer to the trend line. The 95% confidence interval is, consequently, much smaller. Here the trend line slope is approximately 0.8. The offset term, wherein the trend line is given by y=x*slope+offset, is approximately 0.0. The compensation to be applied to the data, ignoring the confidence calculations, would, therefore, be a multiplication by 1/0.8=1.25. Given the very tight confidence intervals, the system of the present invention determines that the appropriate compensation term is at least approximately this multiplicative factor of 1.25.

In FIG. 4, on the other hand, the data are more variable, with a consequently larger confidence interval. Therefore, the computed compensation is not evaluated directly from the trend line 40, but is a fraction of this value. For instance, if the slope were 0.8, then the computed nomogram would not include a compensation term of 1.25, but some value between 1.0 and 1.25.

In summary, then, if the confidence is very high, the embodiments of the system of this invention compensate for all or most of the observed trend; otherwise, the amount of compensation is reduced as a function of this confidence and statistical distribution.

The embodiments of the system and method of the present invention can also account for other factors. In refractive surgery it is desirable that all patients have optimal outcomes. However, owing to the nature of the process and variation in healing among individuals, this is not realistic. Patients are sometimes over-corrected by receiving more treatment than needed, or under-corrected by receiving less treatment than needed. Typically the latter is preferred, since additional tissue can always be removed by a subsequent surgery, but additional treatment following an over-correction can demand a larger removal of tissue.

Hence, in addition to the confidence-based adjustments to the nomogram, additional adjustments can be made as appropriate, so as to bias the nomogram such that any expected residual error trend will tend towards under-correction rather than over-correction. The degree to which the bias should be applied is directly impacted by the confidence in the data, so that with high confidence there is less need for under-correction bias.

Embodiments of this invention can provide for an additional modification to the nomogram. It is known that the eye does not respond to treatment as linearly or simply as expected based solely upon laser delivery calculations. For example, if one observes (with high confidence) a 10% undercorrection, increasing the treatment by 10% does not necessarily yield optimal outcomes. Based upon the characteristics of the treatment and the healing response of the eye, more or less change in outcomes may be observed. This factor can also be compensated for by modifying the nomogram accordingly. The conservative approach is to reduce the amount of correction applied such that the nomogram calculation is effectively "damped," as in a servo response system. This results in an optimal nomogram being obtained over time, but with the initial nomogram being somewhat conservative.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the system and method illustrated and described herein are by way of example, and the scope of the invention is not limited to the exact details disclosed herein.

Having now described the invention, the construction, the operation and use of preferred embodiment thereof, and the advantageous new an useful results obtained thereby, the new and useful constructions, and reasonable mechanical equivalents thereof obvious to those skilled in the art, are set forth in the appended claims.

What is claimed is:

1. A method for optimizing a prescription for laser-ablation corneal treatment comprising the steps of:
    receiving a current measured correction prescription for a current patient;
    accessing a database of treatment outcomes on a plurality of previously treated patients, each treatment outcome comprising a desired correction based upon a measured correction prescription and a postoperative actual correction of a previously treated patient;
    calculating, by a processor, from the treatment outcomes in the database a distribution of data points as a function of correction level;
    calculating, by the processor, from the data point distribution a slope and a statistically based offset using a regression analysis that characterizes the data point distribution, the slope and offset corresponding to a trend line;
    calculating, by the processor, from the data point distribution a confidence interval of the data points relative to the trend line using a predetermined confidence level;
    calculating, by the processor, from the slope and the offset of the data point distribution a compensation value used to adjust the current measured correction prescription, the compensation value adjusting the current measured correction prescription to a greater extent if there is a smaller confidence interval to a lesser extent if there is a larger confidence interval; and
    outputting the compensation value for use in performing a refractive procedure.

2. The method recited in claim 1, wherein the step of calculating a statistically based offset comprises performing a least-squares fit to calculate the offset.

3. The method recited in claim 1, wherein the step of calculating a statistically based offset comprises performing a minimum least-squares error fit to calculate the offset.

4. The method recited in claim 1, wherein the predetermined confidence level is in a range of 90 to 95%.

5. A system for optimizing a prescription for laser-ablation corneal treatment comprising:
    a processor;
    a database of treatment outcomes on a plurality of previously treated patients, each treatment outcome comprising a desired correction based upon a measured correction prescription and a postoperative actual correction of a previously treated patient, the database in signal communication with the processor;
    a software package resident on a medium readable by the processor, the software package comprising code segments adapted to:
        receive a current measured correction prescription for a current patient;
        access the database of treatment outcomes;
        calculate, by a processor, from the accessed treatment outcomes a distribution of data points as a function of correction level;
        calculate, by the processor, from the data point distribution a slope and a statistically based offset using a regression analysis that characterizes the data point distribution, the slope and offset corresponding to a trend line;
        calculate, by the processor, from the data point distribution a confidence interval of the data points relative to the trend line using a predetermined confidence level;
        calculate, by the processor, from the slope and the offset of the data point distribution a compensation value used to adjust the current measured correction prescription, the compensation value adjusting current measured correction prescription to a greater extent if there is a smaller confidence interval and to a lesser extent if there is a larger confidence interval; and
        output the compensation value for use in performing a refractive procedure.

6. The system recited in claim 5, wherein the code segment for calculating a statistically based offset comprises a code segment for performing a least-squares fit to calculate the offset.

7. The system recited in claim 5, wherein the code segment for calculating a statistically based offset comprises a code segment for performing a minimum least-squares error fit to calculate the offset.

8. The system recited in claim 5, wherein the predetermined confidence level is in a range of 90 to 95%.

9. A method for performing a refractive procedure on a patient comprising the steps of:
    measuring a current patient to determine a current correction needed to achieve a desired vision improvement, the current correction achievable with a refractive procedure;
    accessing a database of treatment outcomes on a plurality of previously treated patients, each treatment outcome comprising a desired correction based upon a measured correction prescription and a postoperative actual correction of a previously treated patient;
    calculating, by a processor, from the treatment outcomes in the database a distribution of data points as a function of correction level;
    calculating, by the processor, from the data point distribution a slope and a statistically based offset using a regression analysis that characterizes the data point distribution, the slope and offset corresponding to a trend line;
    calculating, by the processor, from the data point distribution a confidence interval of the data points relative to the trend line using a predetermined confidence level;
    calculating, by the processor, from the slope and the offset of the data point distribution a compensation value used to adjust the current correction, the compensation value adjusting the current correction to a greater extent if there is a smaller confidence interval and to a lesser extent if there is a larger confidence interval; and performing the refractive procedure on the current patient using the compensation value.

10. The method recited in claim 9, wherein the step of calculating a statistically based offset comprises performing a least-squares fit to calculate the offset.

11. The method recited in claim 9, where the step of calculating a statistically based offset comprises performing a minimum least-squares error fit to calculate the offset.

12. The method recited in claim 9, where the predetermined confidence level is in a range of 90 to 95%.

13. A method comprising:

accessing a database of a plurality of treatment outcomes of a plurality of previously treated patients, wherein each treatment outcome comprises a desired correction prescription and a postoperative actual correction of a previously treated patient;

calculating, by a processor, from the treatment outcomes in the database a distribution of data points as a function of correction level;

performing a regression analysis to characterize the distribution of data points and to determine a trend line;

calculating, by the processor, from the regression analysis a confidence interval of the distribution of data points relative to the trend line according to a predetermined confidence level;

calculating, by the processor, from the regression analysis an offset and a slope;

calculating, by the processor, from the slope and the offset of the data point distribution a compensation value used to adjust a new desired correction prescription, the compensation value adjusting the new desired correction prescription to a greater extent if there is a smaller confidence interval and to a lesser extent if there is a larger confidence interval; and outputting the compensation value for use in determining a refractive procedure.

14. The method recited in claim 13, further comprising:

adjusting the new desired correction prescription using the compensation value;

obtaining a new postoperative actual correction resulting from the new desired correction prescription; and adding the new desired correction prescription and the new postoperative actual correction into the database as a new treatment outcome.

15. The method recited in claim 13, wherein calculating the compensation value further comprises:

reducing the compensation value based on the confidence interval.

16. The method recited in claim 13, wherein calculating the compensation value further comprises:

if the confidence interval is smaller than a predetermined amount, calculating the compensation value from the slope and the offset; and if the confidence interval is larger than a predetermined amount, calculating the compensation value from the slope and the offset and reducing the calculated compensation value.

17. The method recited in claim 13, wherein the predetermined confidence level is in a range of 90 to 95%.

* * * * *